United States Patent
Kang (10) Patent No.: US 9,989,503 B2
(45) Date of Patent: Jun. 5, 2018

(54) APPARATUS FOR QUANTITATIVELY ANALYZING GAS COMPONENTS WITH AUTOMATIC FEED CONTROL FUNCTION OF GAS

(71) Applicant: KOREA RESEARCH INSTITUTE OF STANDARDS AND SCIENCE, Daejeon (KR)

(72) Inventor: Namgoo Kang, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 114 days.

(21) Appl. No.: 15/080,228

(22) Filed: Mar. 24, 2016

(65) Prior Publication Data
US 2016/0282316 A1    Sep. 29, 2016

(30) Foreign Application Priority Data

Mar. 24, 2015 (KR) .................. 10-2015-0040452

(51) Int. Cl.
*G01N 30/32* (2006.01)
*G01N 30/02* (2006.01)

(52) U.S. Cl.
CPC ....... *G01N 30/32* (2013.01); *G01N 2030/025* (2013.01); *G01N 2030/328* (2013.01)

(58) Field of Classification Search
CPC ............. G01N 30/32; G01N 2030/025; G01N 2030/328
USPC ............ 73/23.42, 23.41, 23.35, 61.55, 61.56
See application file for complete search history.

(56) References Cited

U.S. PATENT DOCUMENTS

| | | | | |
|---|---|---|---|---|
| 5,714,676 A * | 2/1998 | Hase | ...................... | G01N 30/06 73/23.41 |
| 6,668,623 B2 * | 12/2003 | Tani | ...................... | G01N 30/06 210/198.2 |
| 2013/0327692 A1 * | 12/2013 | Brann | .................... | B01D 15/16 210/141 |
| 2015/0040648 A1 * | 2/2015 | Matsubara | ........... | B01D 15/265 73/61.56 |

FOREIGN PATENT DOCUMENTS

| KR | 1020030067220 A | 8/2003 |
|---|---|---|
| KR | 1020090069360 A | 7/2009 |
| KR | 101447499 B1 | 10/2014 |

* cited by examiner

*Primary Examiner* — Manish S Shah
*Assistant Examiner* — Suman K Nath
(74) *Attorney, Agent, or Firm* — McCoy Russell LLP (57) ABSTRACT

Provided is an apparatus for quantitatively analyzing one or more gas components contained in a gas sample. More particularly, an apparatus for quantitatively analyzing gas components with an automatic feed control function of a gas, includes a multi-position valve, a pump, and a control part controlling the multi-position valve and the pump, such that the apparatus for quantitatively analyzing gas components may allow a professional worker performing analysis to secure an efficient research time while ensuring accuracy at the level equivalent to analysis results by a highly skilled professional worker regardless of proficiency of a newly employed person being in charge of quantitative analysis of the gas components of the gas sample in a sample bag.

1 Claim, 5 Drawing Sheets

| Sample | C-20-b | B-20 | C-20-b | C-10 | C-20-b | B-10 | C-20-b | C-40 | C-20-b | B-40 | C-20-b |
|---|---|---|---|---|---|---|---|---|---|---|---|
| Gravimetric concentration (μmol/mol) | 19.9 | 19.9 | 19.9 | 10.1 | 19.9 | 10.1 | 19.9 | 39.5 | 19.9 | 39.5 | 19.9 |
| MPV position | 1 | 2 | 1 | 3 | 1 | 4 | 1 | 5 | 1 | 6 | 1 |
| peak area 1 | 87.60 | 88.21 | 87.80 | - | - | - | - | - | - | - | - |
| peak area 2 | 87.76 | 88.10 | 88.10 | - | - | - | - | - | - | - | - |
| peak area 3 | 87.81 | 90.58 | 88.17 | - | - | - | - | - | - | - | - |
| peak area 4 | 87.75 | 87.06 | 88.18 | - | - | - | - | - | - | - | - |
| peak area 5 | 87.98 | 86.96 | 88.16 | 47.68 | 85.97 | 44.53 | 88.13 | 174.83 | 88.46 | 172.35 | 88.27 |
| peak area 6 | 88.02 | 87.15 | 88.10 | 46.93 | 86.43 | 44.60 | 88.23 | 174.83 | 88.48 | 172.38 | 88.23 |
| peak area 7 | 88.18 | 87.23 | 88.19 | 46.48 | 86.91 | 44.53 | 88.18 | 175.22 | 88.48 | 172.41 | 88.31 |
| peak area 8 | 88.35 | 87.24 | 88.30 | 46.23 | 87.09 | 44.61 | 88.29 | 175.02 | 88.32 | 172.31 | 88.22 |
| peak area 9 | 88.20 | 87.22 | 88.31 | 45.84 | 87.58 | 44.55 | 88.35 | 175.02 | 88.35 | 172.35 | 88.07 |
| peak area 10 | 88.20 | 87.34 | 88.33 | 45.74 | 87.48 | 44.62 | 88.25 | 175.03 | 88.37 | 172.36 | 88.16 |
| peak area 11 | 88.20 | 87.40 | 88.37 | 45.56 | 87.67 | 44.56 | 88.27 | 175.07 | 88.34 | 172.95 | 88.17 |
| peak area 12 | 88.17 | 87.10 | 88.42 | 45.45 | 87.58 | 44.60 | 88.25 | 175.05 | 88.37 | 172.33 | 88.26 |
| peak area 13 | 88.34 | 87.24 | 88.21 | 45.36 | 87.79 | 44.56 | 88.29 | 175.40 | 88.28 | 172.38 | 88.13 |
| peak area 14 | 88.35 | 87.38 | 88.36 | 45.23 | 87.85 | 44.43 | 88.48 | 175.14 | 88.42 | 172.23 | 88.16 |
| peak area 15 | 88.30 | 87.15 | 88.36 | 45.25 | 87.84 | 44.52 | 88.14 | 175.29 | 88.29 | 172.48 | 88.15 |
| PA average | 88.08 | 87.56 | 88.22 | 45.98 | 87.29 | 44.56 | 88.26 | 175.08 | 88.38 | 172.41 | 88.19 |
| PA STD | 0.25 | 0.91 | 0.16 | 0.78 | 0.62 | 0.05 | 0.10 | 0.17 | 0.07 | 0.19 | 0.07 |
| PA RSD (%) | 0.28 | 1.04 | 0.18 | 1.70 | 0.71 | 0.12 | 0.11 | 0.10 | 0.08 | 0.11 | 0.08 |
| Reponse factor | 4.43 | 4.40 | 4.43 | 4.55 | 4.39 | 4.41 | 4.44 | 4.43 | 4.44 | 4.36 | 4.43 |
| RF average | | 4.430 | | 4.410 | | 4.411 | | 4.438 | | 4.436 | |
| Analytical concentration (μmol/mol) | | 19.77 | | 10.43 | | 10.10 | | 39.45 | | 38.86 | |
| Absolute difference in concentration (μmol/mol) | | 0.13 | | -0.33 | | 0.00 | | 0.05 | | 0.64 | |
| Relative difference in concentration (%) | | 0.67 | | -3.23 | | -0.01 | | 0.13 | | 1.61 | |

| Sample | C-20-b | B-20 | C-20-b | B-10 | C-20-b | B-10 | C-20-b | B-40 | C-20-b | B-40 | C-20-b |
|---|---|---|---|---|---|---|---|---|---|---|---|
| Gravimetric concentration (umol/mol) | 20.0 | 20.0 | 20.0 | 10.1 | 20.0 | 10.1 | 20.0 | 39.5 | 20.0 | 39.5 | 20.0 |
| peak area 1 | 81.80 | 81.54 | 82.06 | 41.86 | - | - | - | - | - | - | - |
| peak area 2 | 81.69 | 81.89 | 81.94 | 41.64 | 81.96 | 41.35 | 81.58 | 160.98 | 82.62 | 161.95 | 82.89 |
| peak area 3 | 81.80 | 81.85 | 82.04 | 41.64 | 82.03 | 41.46 | 81.81 | 161.53 | 82.36 | 162.09 | 82.59 |
| peak area 4 | 81.68 | 81.89 | 82.19 | 41.68 | 82.05 | 41.47 | 82.00 | 161.89 | 82.01 | 162.01 | 82.55 |
| peak area 5 | 81.80 | 81.71 | 82.03 | 41.58 | 82.13 | 41.51 | 82.12 | 161.78 | 82.03 | 162.11 | 82.54 |
| peak area 6 | 81.72 | 81.55 | 81.98 | 41.77 | 83.59 | 41.43 | 82.04 | 161.98 | 82.21 | 161.9 | 82.38 |
| peak area 7 | 81.95 | - | 82.02 | 41.44 | 82.35 | 41.25 | 81.96 | 162.23 | 82.12 | 161.9 | 82.49 |
| peak area 8 | | | | | 82.21 | | | 162.35 | 82.10 | 161.8 | 82.64 |
| peak area 9 | | | | | | | | 162.33 | 82.00 | | 82.44 |
| PA average | 81.78 | 81.47 | 82.04 | 41.66 | 82.33 | 41.41 | 81.92 | 161.88 | 82.18 | 161.97 | 82.57 |
| PA STD | 0.09 | 0.72 | 0.08 | 0.13 | 0.57 | 0.10 | 0.19 | 0.46 | 0.21 | 0.11 | 0.16 |
| PA RSD (%) | 0.11 | 0.89 | 0.10 | 0.32 | 0.69 | 0.23 | 0.24 | 0.29 | 0.26 | 0.07 | 0.19 |
| Reponse factor | 4.09 | 4.07 | 4.10 | 4.12 | 4.12 | 4.10 | 4.10 | 4.10 | 4.11 | 4.10 | 4.13 |
| RF average | | 4.095 | | 4.107 | | 4.106 | | 4.102 | | 4.119 | |
| Analytical concentration (umol/mol) | | 19.89 | | 10.14 | | 10.09 | | 39.46 | | 39.32 | |
| Absolute difference in concentration (umol/mol) | | 0.11 | | -0.04 | | 0.01 | | 0.04 | | 0.18 | |
| Relative difference in concentration (%) | | 0.53 | | -0.43 | | 0.15 | | 0.1 | | 0.44 | |

FIG. 5

APPARATUS FOR QUANTITATIVELY ANALYZING GAS COMPONENTS WITH AUTOMATIC FEED CONTROL FUNCTION OF GAS

CROSS-REFERENCE TO RELATED APPLICATIONS

This application claims priority under 35 U.S.C. § 119 to Korean Patent Application No. 10-2015-0040452, filed on Mar. 24, 2015, in the Korean Intellectual Property Office, the disclosure of which is incorporated herein by reference in its entirety.

TECHNICAL FIELD

The following disclosure relates to an apparatus for quantitatively analyzing one or more gas components contained in a gas sample, and more particularly, to an apparatus for quantitatively analyzing gas components with an automatic feed control function of a gas, provided with a multi-position valve, a pump transferring a gas sample in a sample bag to a gas chromatograph, and a control part controlling the multi-position valve and the pump.

BACKGROUND

The present invention relates to a technology for improving operation convenience of an apparatus while maintaining accuracy of gas component analysis results at the time of using gas component separation and analysis equipment for quantitatively analyzing gas components of a gas sample stored in a sample bag.

In general, a gas chromatograph and a high-pressure gas cylinder in which a standard gas is stored are used in chemical analysis laboratories of various environmental fields (an atmospheric environment, an energy environment, an industrial environment, an agricultural environment, a waste environment, and a medical environment), in order to quantitatively analyze components of a gas sample. In this case, in order to accurately analyze mole fractions of the gas components of the gas sample, a process of introducing the gas sample stored in the sample bag and a high-pressure gas (standard gas) for comparative analysis with the gas sample into the gas chromatograph one by one and introducing another gas sample and the standard gas in the gas chromatograph when the analysis is completed after introduction should be repetitively performed. At this time, since a pressure of the gases introduced into the gas chromatograph during a process of alternately analyzing the gas sample and the standard gas has a large influence on analysis accuracy of unknown mole fractions of the gas components stored in the sample bag, a technology capable of performing quantitative analysis while maintaining the same introduction pressure has been required.

As the related art, a technology of adjusting an introduction pressure at the time of introducing a gas sample or a standard gas in gas chromatograph has been disclosed in Korean Patent No. 1447499.

However, this technology still requires a skilled professional worker to operate an analysis apparatus such that this technology has the following problems in view of practical use. First, if the professional worker is replaced, proficiency is changed, reproducibility of analysis results may be significantly decreased, and thus quality of the analysis result may be deteriorated. Second, since the professional worker requires a lot of time in order to perform a simple repetitive work, productivity may be deteriorated.

RELATED ART DOCUMENT

Patent Document (Patent Document 1) Korean Patent No. 1447499

SUMMARY

An embodiment of the present invention is directed to providing an apparatus for quantitatively analyzing gas components capable of maintaining analysis quality at a predetermined level regardless of proficiency of a professional worker in quantitatively analyzing the gas components.

In one general aspect, an apparatus for quantitatively analyzing gas components with an automatic feed control function of a gas includes: a gas chromatograph analyzing a concentration of an introduced gas when the gas is introduced; a multi-position valve having a plurality of valves and one hole, formed so that when one valve is opened, the other valves are all closed, and discharging gas introduced through the valve in an open state to the gas chromatograph through the hole; a pump connected to the chromatograph and sucking the gas discharged from the hole of the multi-position valve to the gas chromatograph; a control part obtaining information on an analysis initiation point in time, an analysis termination point in time, and a resting period therebetween from the gas chromatograph, and controlling operations of the pump and the multi-position valve using the information; and a sample bag connected to the valve of the multi-position valve and storing the gas sample to be analyzed by the gas chromatograph.

The apparatus for quantitatively analyzing gas components may further include a high-pressure gas cylinder connected to the valve of the multi-position valve and storing a standard gas.

The control part may control suction strength of the pump using information on pressure of the gas sample in the sample bag.

The apparatus for quantitatively analyzing gas components may further include a gas flowing tube having one end connected to the hole of the multi-position valve and the other end connected to the gas chromatograph to transfer the gas discharged from the hole of the multi-position valve to the gas chromatograph; and a gas pressure regulator provided on the gas flowing tube to regulate a pressure of the gas flowing through the gas flowing tube.

The apparatus for quantitatively analyzing gas components may further include a mass flow rate controller provided between the gas pressure regulator on the gas flowing tube and the gas chromatograph to control a mass flow rate of the gas introduced into the gas chromatograph.

Other features and aspects will be apparent from the following detailed description, the drawings, and the claims.

BRIEF DESCRIPTION OF THE DRAWINGS

FIG. 4 illustrates experimental results obtained using the apparatus for quantitatively analyzing gas components with a automatic feed control function of a gas according to the exemplary embodiment of the present invention.

DETAILED DESCRIPTION OF MAIN ELEMENTS

100: Gas chromatograph
200: Pump
300: Mass flow rate controller
310: Mass flow rate input and display device
400: Gas pressure regulator
411: First pressure display device
412: Second pressure display device
421: First pressure gauge
422: Second pressure gauge
500: Multi-position valve
501, 502, 503, 504, 505, 506: Valve
507: hole
510: Back-flow suppressing valve
520: Sample bag
530: High-pressure gas cylinder
600: Control part

DETAILED DESCRIPTION OF EMBODIMENTS

The present invention may be variously modified and have various types, and specific embodiments of the present invention will be described in detail with reference to the accompanying drawing. However, the present invention is not limited to the exemplary embodiments described herein, but all of the modifications, equivalents, and substitutions within the spirit and scope of the present invention are also included in the present invention.

In describing each of the drawing, similar components will be denoted by similar reference numerals. Further, when it is determined that the detailed description of the known art related to the present invention may obscure the gist of the present invention, the detailed description thereof will be omitted.

For example, the 'first' component may be named the 'second' component and the 'second' component may also be similarly named the 'first' component, without departing from the scope of the present invention.

The term "and/or" is used as a meaning including a combination of a plurality of details associated with each other or any one of the plurality of details associated with each other.

It is to be understood that when one component is referred to as being "connected to" or "coupled to" another component, it may be "directly connected to" or "directly coupled to" another element, or be connected to or coupled to another element, having the other element intervening therebetween.

On the contrary, it is to be understood that when one component is referred to as being "directly connected to" or "directly coupled to" another element, there is no element intervening therebetween.

Terms used in the present specification are used in order to describe specific exemplary embodiments rather than limiting the present invention.

Singular forms used in the specification are intended to include plural forms unless the context clearly indicates otherwise. Terms such as "include", "have", and the like, used in the present specification will imply the existence of stated features, numbers, steps, operations, configuration elements, components, or a combination thereof, but do not exclude presence or addition of one or more other features, numbers, steps, operations, configuration elements, components, or a combination thereof Unless otherwise defined herein, technical and scientific terms used in the present specification have the same meanings as those understood by those skilled in the art to which the present invention pertains.

Generally used terms as defined in a dictionary should be construed as meanings equal to contextual meanings in the related art and not construed as ideal or excessively formal meanings as long as the meanings are not clearly defined in the present specification.

Hereinafter, a gas components quantitative analysis apparatus with an automatic feed control function of gas according to an exemplary embodiment of the present invention will be described in detail with reference to the accompanying drawings.

Figure 1:
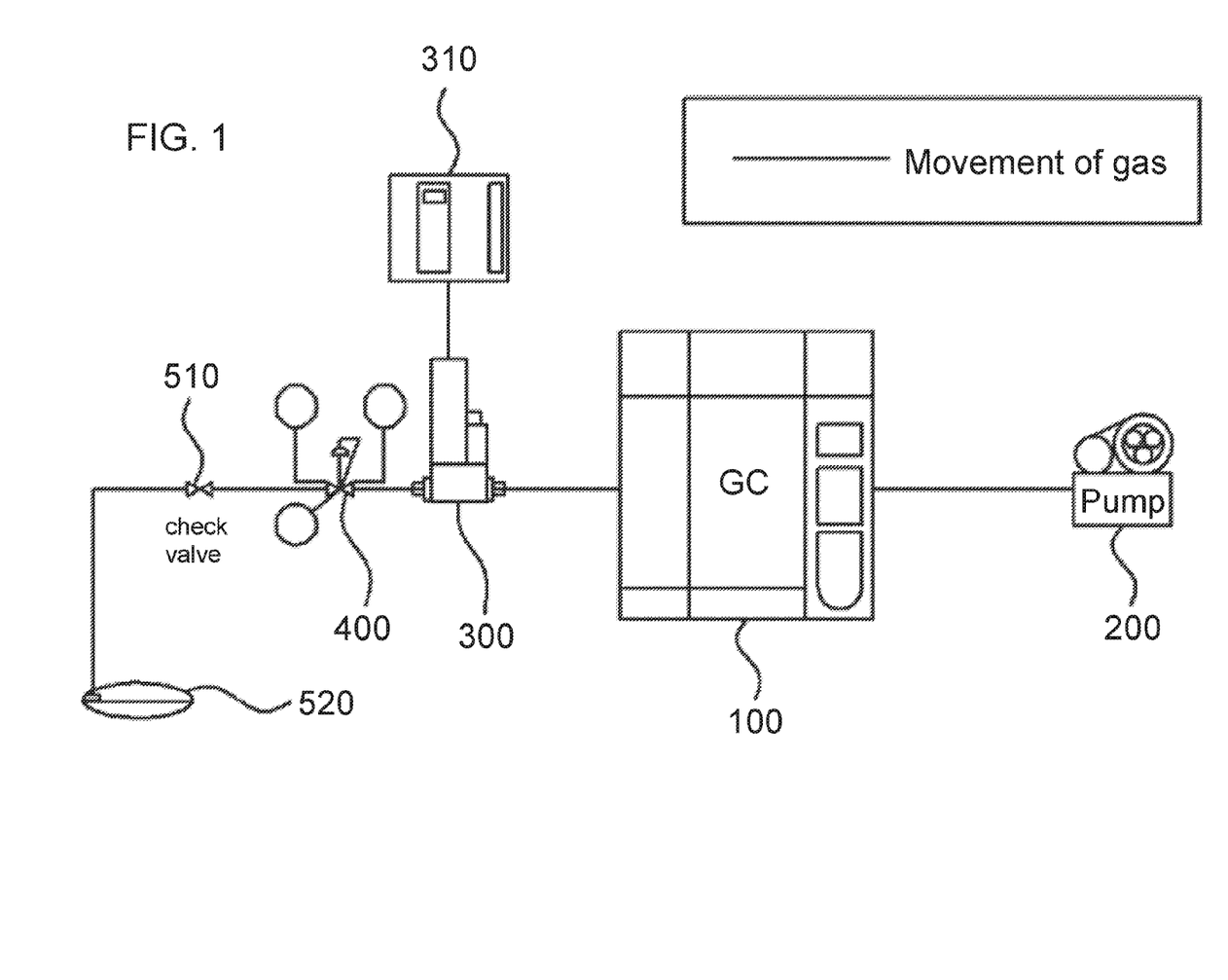
FIG. 1 is a schematic view for describing a case in which a gas sample in a sample bag is manually introduced into an apparatus for quantitatively analyzing gas components.
Figure 2:
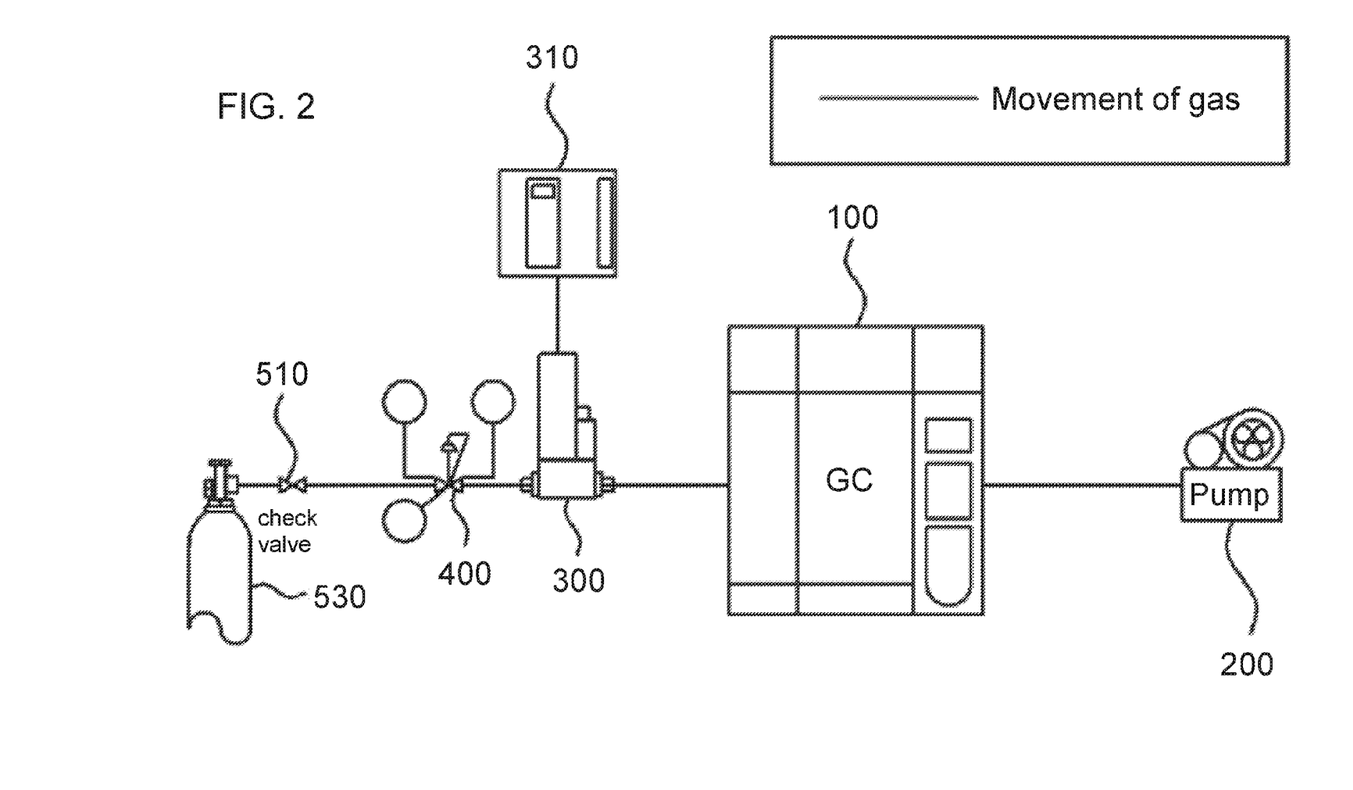
FIG. 2 is a schematic view for describing a case in which a standard gas stored in a high-pressure gas cylinder is manually introduced into the apparatus for quantitatively analyzing gas components.

FIG. 1 is a schematic view for describing a case in which a gas sample in a sample bag is manually introduced into an apparatus for quantitatively analyzing gas components, and FIG. 2 is a schematic view for describing a case in which a standard gas stored in a high-pressure gas cylinder is manually introduced into the apparatus for quantitatively analyzing gas components. Referring to FIGS. 1 and 2, the apparatus for quantitatively analyzing gas components may include a gas chromatograph 100, a pump 200, a mass flow rate controller 300, a mass flow rate input and display device 310, a gas pressure regulator 400, and a back-flow suppressing value 510. Further, the apparatus for quantitatively analyzing gas components may include a sample bag 520 in which a gas sample of which components will be analyzed is stored or a high-pressure gas cylinder 530 in which a standard gas is stored.

In addition, gas flowing tubes are provided between the sample bag 520 and the gas chromatograph 100 (or the high-pressure gas cylinder 530 and the gas chromatograph 100), and between the gas chromatograph 100 and the pump 200, respectively.

The gas chromatograph 100 may include a sample introduction part having a sample loop, an analysis part, and a discharge part, and in order to analyze the gas components of the gas sample to be introduced, a column may be provided. Since the structure and operations of the gas chromatograph are already applied to industrial fields, a detailed description thereof will be omitted.

The pump 200 may be connected to the discharge part of the gas chromatograph 100, and suck the standard gas (or the gas sample) stored in the high-pressure gas cylinder 530 (or the sample bag 520) into the sample introduction part of the gas chromatograph.

The mass flow rate controller 300 is connected to the high-pressure gas cylinder 530 or the sample bag 520 to adjust a mass flow rate of the gas introduced into the sample introduction part of the gas chromatograph 100. Here, the mass flow rate controller 300 means a device regulating the mass flow rate, wherein the mass flow rate is a mass flowing for unit time per unit cross-sectional area ((average flow rate)*(fluid density)).

A mass flow rate input and display device 310 provides an interface and a screen through which the mass flow rate may be set to the mass flow rate controller 300.

The gas pressure regulator 400 is a device connected between the high-pressure gas cylinder 530 and the mass flow rate controller 300 to lower pressure of the gas to low pressure, and in the case of connecting a container in which a normal-pressure gas is stored, such as the sample bag 520, the gas pressure regulator may not be used.

The pressure of the gases introduced into the sample introduction part of the gas chromatograph may be controlled by controlling the mass flow rate controller 300 and the gas pressure regulator 400.

The back-flow suppressing valve 510 is connected between high-pressure gas cylinder 530 and the gas pressure regulator 400 in order to prevent back-flow of a high-pressure gas (the standard gas), and in the case of connecting the container in which the normal-pressure gas is stored, such as the sample bag 520, the back-flow suppressing valve 510 may not be used.

The high-pressure gas cylinder 530 is a container capable of storing the high-pressure gas, and the standard gas may be stored therein. In this case, the standard gas may be composed of gas containing analysis target components at a predetermined mole fraction and may be used in order to form standard for interpreting gas chromatography results of the gas sample. That is, at the time of actual analysis, mole fractions of the gas components of the gas sample in the sample bag, which are the analysis target components, may be quantitatively calculated by performing gas chromatography on both of the standard gas and the gas sample and comparing the results with each other.

The sample bag 520 means a container in which the gas sample to be analyzed is stored. As the sample bag 520, a portable plastic bag is mainly used, and the sample bag 520 may be made of a fluorine based polymer such as polyvinyl fluoride (PVF, product name: Tedlar®) or polyvinylidene difluoride (PVDF, product name: Kynar®).

In order to manually perform component quantitative analysis on the gas sample in the sample bag, the following three-step process may be performed.

In step 1, the apparatus for quantitatively analyzing gas components may be installed and the sample bag 520 in which the gas sample is stored may be connected thereto as illustrated in FIG. 1. Next, the gas sample may be introduced into the gas chromatograph 100 by operating the pump 200, and a pressure of the gas sample flowing through a gas flowing tube may be controlled to a preset value using the mass flow rate controller 300. In step 1, finally, a chromatogram may be analyzed using the gas chromatograph 100.

In step 2, the apparatus for quantitatively analyzing gas components may be installed and high-pressure gas cylinder 530 in which the standard gas is stored may be connected thereto as illustrated in FIG. 2. Next, the standard gas may be introduced into the gas chromatograph 100 by operating the pump 200, and the pressure of the standard gas flowing through the gas flowing tube may be controlled to a preset value using the mass flow rate controller 300. In step 2, finally, a chromatogram may be analyzed using gas chromatograph.

In step 3, the mole fractions of the gas components of the gas sample in the sample bag 520 may be calculated by analyzing the chromatograms, which are analysis results of respective steps.

Figure 3:
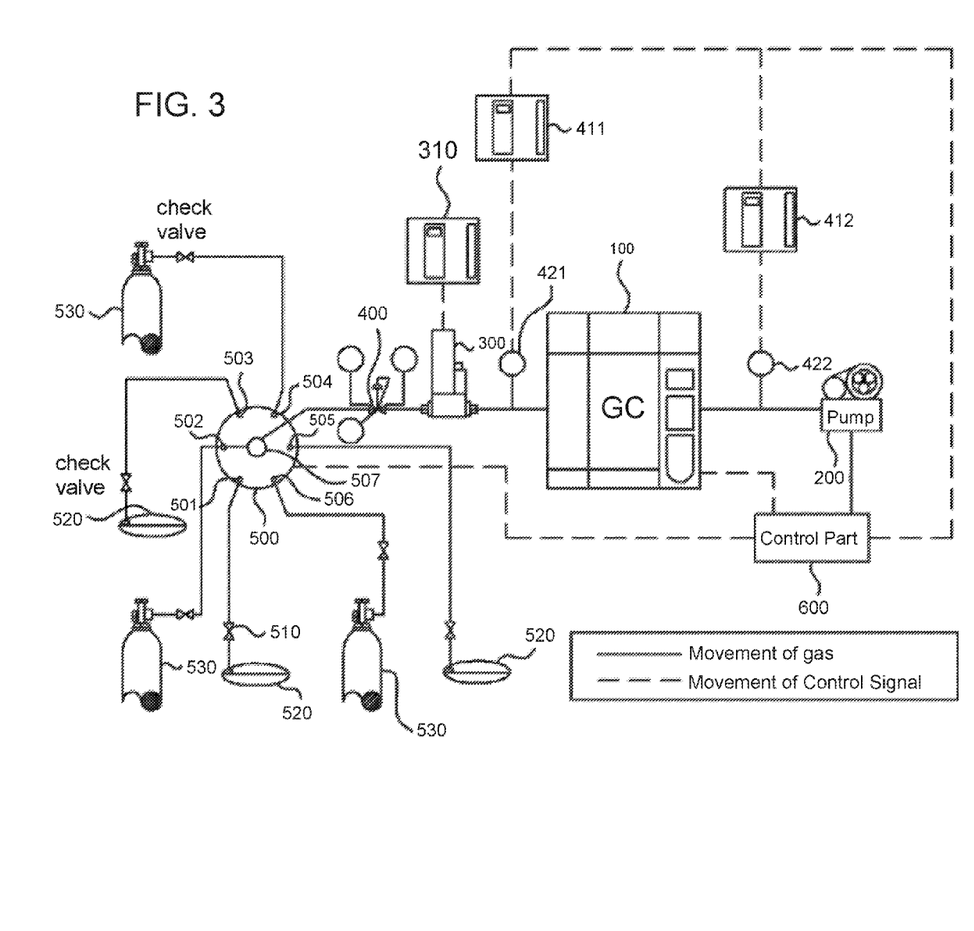
FIG. 3 is a schematic view illustrating an apparatus for quantitatively analyzing gas component with an automatic feed control function of a gas according to an exemplary embodiment of the present invention.

The present invention is implemented by automating a process of connecting the sample bag 520 in which the gas sample is stored in step 1 and a process of connecting the high-pressure gas cylinder 530 in which the standard gas is stored in step 2 using a multi-position valve 500 and adding a control part 600 controlling the multi-position valve 500 and the pump 200 using the analysis initiation point in time and the analysis termination point in time of the gas chromatograph 100, in order to automate the three-step process as described above.

FIG. 3 is a schematic view illustrating an apparatus for quantitatively analyzing gas components with an automatic feed control function of a gas according to an exemplary embodiment of the present invention.

The apparatus for quantitatively analyzing gas components with an automatic feed control function of a gas according to the exemplary embodiment of the present invention may include the gas chromatograph 100, the pump 200, the mass flow rate controller 300, the mass flow rate input and display device 310, the gas pressure regulator 400, the back-flow suppressing value 510, and the gas flowing tube as described above, and further include the multi-position valve 500 and the control part 600.

The multi-position valve 500 may have a plurality of valves 501, 502, 503, 504, 505, 506 and one hole 507, and the multi-position valve 500 is formed so that in the case in which one valve is opened, the other valves are all closed, and gas introduced through the valve 501, 502, 503, 504, 505, 506 in an open state may be discharged to the sample introduction part of the gas chromatograph 100 through the hole 507. Since the multi-position valve 500 as described above is already applied to various industrial fields, a detailed description thereof will be omitted.

Meanwhile, as illustrated in FIG. 3, gas flowing tubes are formed between each of the sample bags 520 and the multi-position valve 500, and are also formed between each of the high-pressure gas cylinders 530 and the multi-position valve 500.

Further, a gas flowing tube is formed between the multi-position valve 500 and the gas chromatograph 100, and one end of the gas flowing tube is connected to the hole 507 of the multi-position valve 500 and the other end thereof is connected to the sample introduction part of the gas chromatograph 100, such that the gas discharged from the hole 507 of the multi-position valve 500 may be introduced into the sample introduction part of the gas chromatograph 100.

The mass flow rate controller 300 and the gas pressure regulator 400 may be disposed on the gas flowing tube, and the gas discharged from the multi-position valve 500 may sequentially pass through the mass flow rate controller 300 and the gas pressure regulator 400 to thereby be introduced into the sample introduction part of the gas chromatograph 100.

The control part 600 may receive information on an analysis initiation point in time, an analysis termination point in time, and a resting period therebetween from the gas chromatograph 100 to generate a control signal controlling an operation of the multi-position valve 500 and an operation of the pump 200, and control the multi-position valve 500 and the pump 200 according to the control signal.

In the case in which a multi-position valve 500 including six valves 501, 502, 503, 504, 505, 506 is provided in the apparatus for quantitatively analyzing gas components according to the exemplary embodiment of the present invention, control signals generated by the control part in three steps may be the same as those illustrated in the following <Table 1>. In this case, when a sample bag in which a gas sample A is stored is connected to a first valve 501 of the multi-position valve 500, a high-pressure gas cylinder in which a standard gas A is stored is connected to a second valve 502 of the multi-position valve 500, a sample bag in which a gas sample B is stored is connected to a third valve 503 of the multi-position valve 500, a high-pressure gas cylinder in which a standard gas B is stored is connected to an fourth valve 504 of the multi-position valve 500, a sample bag in which a gas sample C is stored is connected to a fifth valve 505 of the multi-position valve 500, and a high-pressure gas cylinder in which a standard gas C is stored is connected to a sixth valve 506 of the multi-position valve 500, analysis of mole fractions of the gas components of each of the gas samples (that is, the gas samples A, B, and C) is attempted.

As illustrated in the following Table 1, since in step 3, the mole fractions of the gas samples in the sample bag are calculated from known mole fractions of the standard gas by comparing the calculated chromatogram results, the gas chromatograph 100 does not operate, and there may be no control signal for the pump 200 or the multi-position valve 500. Further, due to characteristics of the multi-position valve 500, when one valve is opened, the other valves are all closed.

TABLE 1

| Process | Operation State of Gas Chromatograph | Multi-position Valve Control Signal | Pump Control Signal |
|---|---|---|---|
| A-Step 1 | Analysis Initiation Point in Time | Open First Valve-Connect Sample Bag | Pump on |
|  | Analysis Termination Point in Time | — | Pump off |
|  | Resting Period | — | Pump on |
| A-Step 2 | Analysis Initiation Point in Time | Open Second Valve-Connect High-Pressure Gas Cylinder | Pump on |
|  | Analysis Termination Point in Time | — | Pump off |
|  | Resting Period | — | Pump on |
| B-Step 1 | Analysis Initiation Point in Time | Open Third Valve-Connect Sample Bag | Pump on |
|  | Analysis Termination Point in Time | — | Pump off |
|  | Resting Period | — | Pump on |
| B-Step 2 | Analysis Initiation Point in Time | Open Fourth Valve-Connect High-Pressure Gas Cylinder | Pump on |
|  | Analysis Termination Point in Time | — | Pump off |
|  | Resting Period | — | Pump on |
| C-Step 1 | Analysis Initiation Point in Time | Open Fifth Valve-Connect Sample Bag | Pump on |
|  | Analysis Termination Point in Time | — | Pump off |
|  | Resting Period | — | Pump on |
| C-Step 2 | Analysis Initiation Point in Time | Open Sixth Valve-Connect High-Pressure Gas Cylinder- | Pump on |
|  | Analysis Termination Point in Time | — | Pump off |
|  | Resting Period | — | Pump on |
| Step 3 | No relation | No relation | No relation |

A concentration and a pressure of the gas sample stored in the sample bag may have an influence on the control part determining the pump control signal.

That is, in the case of performing gas chromatography on the gas sample stored in the sample bag 520 in order to quantitatively analyze the mole fractions of the gas components of the gas sample and performing gas chromatography on the standard gas stored in the high-pressure gas cylinder 530 to be used for analyzing the mole fractions, the control part 600 controls suction strength of the pump 200 so that pressures of the gas flowing through the gas flowing tube formed between the multi-position valve 500 and the gas chromatograph 100 are the same each other in the two times of gas chromatography, thereby making it possible to minimize an analysis error of the mole fractions.

Since the standard gas stored in the high-pressure gas cylinder 530 is discharged at a predetermined pressure in a high-pressure state through the gas pressure regulator 400, the control part 600 does not need to significantly adjust the suction strength of the pump 200. Unlike this, the control part 600 needs to adjust the suction strength of the pump 200 for analyzing the mole fractions of gas components of the gas sample stored in the sample bag 520.

Since the pressure of the gas sample stored in the sample bag 520 is equal to or just slightly higher than atmospheric pressure, when the suction strength of the pump 200 is low, the gas sample may slowly diffuse to the column of the gas chromatograph 100, or a pre-diffused gas sample filled in the gas flowing tube may flow backward, such that an arrival time of the gas sample to the column may be excessively increased. Due to the above-mentioned phenomenon, analysis conditions of the gas chromatograph may not be satisfied, and as a result, a sensing signal may not be suitably exhibited, or reproducibility may be deteriorated.

Therefore, at the time of performing comparative analysis on the gas sample stored in the sample bag 520 with the standard gas in the high-pressure gas cylinder 530, the control part 600 needs to control the suction strength of the pump 200.

An operation of the control part 600 as described above will be described in detail. First, in a case of introducing the gas sample stored in the sample bag 520 into the gas chromatograph 100, after a pressure of the gas sample flowing through the gas flowing tube formed between the mass flow rate controller 300 and the gas chromatograph 100 is measured by a first pressure gauge 421, and the measured pressure value (a first pressure measured value) is transferred to the control part 600 through a first pressure display device 411.

Thereafter, at the time of introducing the standard gas stored in the high-pressure gas cylinder 530 into the gas chromatograph 100, a pressure of the standard gas flowing through the gas flowing tube formed between the mass flow rate controller 300 and the gas chromatograph 100 is also measured by the first pressure gauge 421, and the measured pressure value (a second pressure measured value) is also transferred to the control part 600 through the first pressure display device 411.

In this case, the control part 600 may control the suction strength of the pump 200 so that the second pressure value is equal to the first pressure value.

That is, the control part 600 may generate a control signal for the suction strength of the pump 200, thereby changing the suction strength of the pump 200 so that the pressure of the gas sample between the mass flow rate controller 300 and the sample introduction part of the gas chromatograph 100 and the pressure of the standard gas therebetween are the same as each other. The control part 600 operates as described above, such that the pressures of the gas sample and the standard gas introduced into the gas chromatograph 100 are the same as each other within a predetermined error level. Therefore, the mole fractions of the gas components of the gas sample may be accurately analyzed.

The control part 600 may control a suction amount of the pump 200 only using the first pressure gauge 421 and the first pressure display device 411. However, a second pressure gauge 422 and a second pressure display device 412 may be additionally provided, thereby making it possible to confirm whether or not a pressure between the gas chromatograph 100 and the pump 200 at the time of analyzing the gas sample and a pressure therebetween at the time of analyzing the standard gas are the same as each other. In this case, since it may be confirmed that the pressure of the gas sample and the pressure of the standard gas are the same as each other in both front and rear ends of the gas chromatograph 100, the mole fractions of the gas components of the gas sample in the sample bag 520 may be more accurately determined.

The control part 600 may be an independent device obtaining information from ChemStation, which is a program for gas chromatograph, or may be a program stored in a medium mounted in the gas chromatograph, modified from ChemStation. Further, the control part 600 may include a relay control system (RCS) for controlling a switch of the pump 200.

After a multi-position valve 500 having six valves 501, 502, 503, 504, 505, 506 and one hole 507 was selected and configured in the apparatus for quantitatively analyzing gas components with an automatic feed control function of a gas according to the exemplary embodiment of the present invention as illustrated in FIG. 3, in order to accurately identify different mole fractions (μmol/mol) of methane stored in three different sample bags B-10, B-20, B-40, an experiment for comparative analysis with the standard gases stored in three different high-pressure gas cylinders C-10, C-20-b, C-40 was performed, thereby obtaining experimental results illustrated in Table of FIG. 4.

In the experiment, a sample bag in which a gas sample (20 μmol/mol in $N_2$) was stored was connected to the first valve 501 and denoted by B-20, and a high-pressure gas cylinder in which methane standard gas (20 μmol/mol in $N_2$) was stored was connected to the second valve 502 and denoted by C-20-b. Here, C-20-b means that a singular value was removed in an analysis process.

In addition, a sample bag in which a gas sample (10 μmol/mol in $N_2$) was stored was connected to the third valve 503 and denoted by B-10, and a high-pressure gas cylinder in which methane standard gas (10 μmol/mol in $N_2$) was stored was connected to the fourth valve 504 and denoted by C-10.

Further, a sample bag in which a gas sample (40 μmol/mol in $N_2$) was stored was connected to the fifth 505 valve and denoted by B-40, and a high-pressure gas cylinder in which methane standard gas (40 μmol/mol in $N_2$) was stored was connected to the sixth valve 506 and denoted by C-40.

As the analysis target gas component used in the experiment, methane ($N_2$ balance, concentration: μmol/mol), which is a representative example of non-adsorptive and non-reactive gas components, was used, and in order to quantitatively analyze the methane component, gas chromatography-flame ionization detector (GCFID) was used. A temperature of a sample introduction part was 100° C., and an internal volume of a sample loop was 1.0 mL. As a column for separating methane, a packed column; Porapak Q (12 ft, 80/100 mesh, stainless steel) was used. An oven temperature was 100° C., an isothermal condition was applied, and a detector temperature was 250° C. A flow rate of transportable gas (nitrogen) in the column was 8 mL/min (8.70 psi), and an entire flow rate was 28 mL/min. A flow rate of fuel gas (hydrogen) in a detector was 60 mL/min, a flow rate of oxidizing gas (air) was 450 mL/min, a make-up flow rate was 10 mL/min, and a flow rate of the sample gas was 100 mL/min. A retention time of the methane component of the chromatogram was 1.742 minutes.

Figure 5:
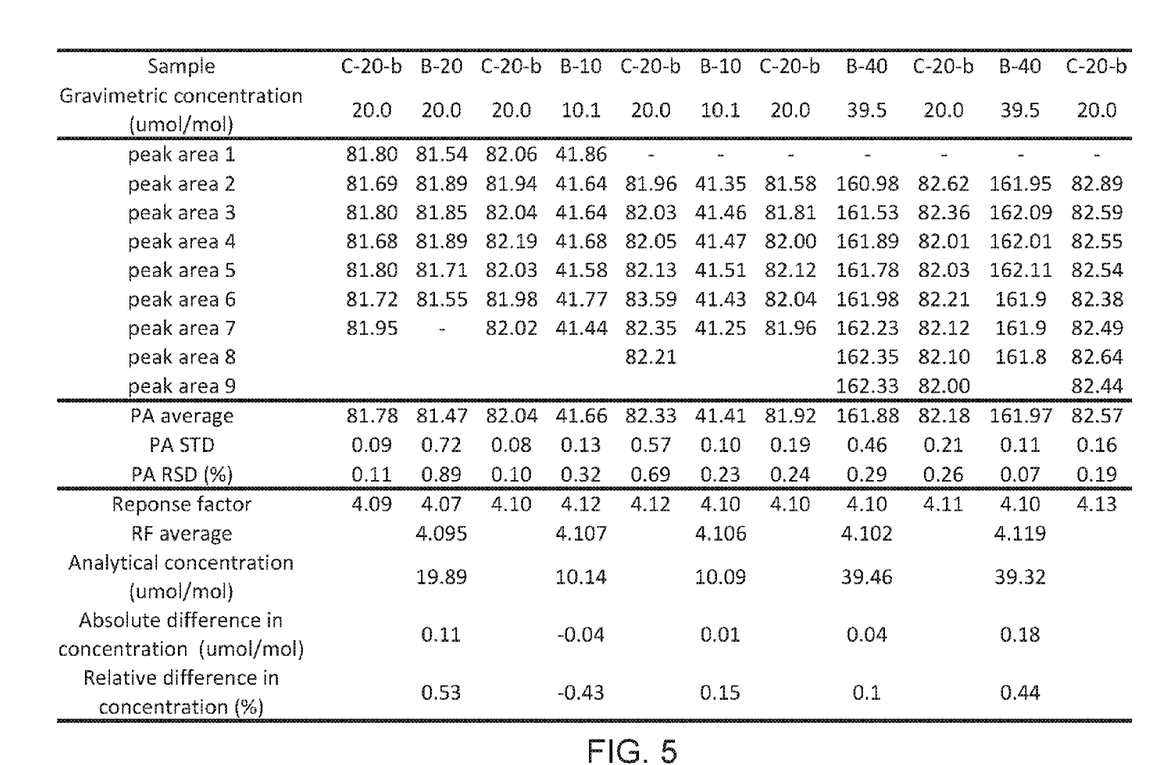
FIG. 5 illustrates experimental results obtained by manually operating the apparatus for quantitatively analyzing gas components according to the related art.

Statistically analyzing the results of FIG. 4, in the case of C-20-b, an uncertainty value of repeatability was 0.08% to 0.71% as a peak area relative standard deviation [PA RSD (%)] in view of the repeatability of analysis of the same sample analysis. This result was equivalent to an uncertainty value (0.10% to 0.69%) of repeatability obtained by a skilled professional worker using a gas components quantitative analysis apparatus according to the related art in experimental results of FIG. 5.

Further, an uncertainty value of analysis reproducibility, which is a response factor relative standard deviation [RF RSD (%)] of the standard gas C-20-b used as a standard for confirming reproducibility, was 0.4%. This result was almost equivalent to an uncertainty value (0.35%) of reproducibility obtained with respect to the same reference sample in the experimental result of FIG. 5. Therefore, it may be confirmed that in the case of using the apparatus for quantitatively analyzing gas components according to the exemplary embodiment of the present invention, it is possible to solve inconvenience of manual analysis while not decreasing accuracy of the mole fraction analysis of the gas components of the gas sample in the sample bag.

The apparatus for quantitatively analyzing gas components with an automatic feed control function of a gas according to the exemplary embodiment of the present invention may provide repeatability and reproducibility equivalent to those obtained by a skilled researcher in view of calculating the mole fractions of the gas components of the gas sample in the sample bag.

As described above, the apparatus for quantitatively analyzing gas components according to the present invention includes the multi-position valve, the pump, and the control part controlling the multi-position valve and the pump, and thus the apparatus for quantitatively analyzing gas components may allow a professional worker performing analysis to secure an efficient research time while ensuring accuracy at the level equivalent to analysis results by a highly skilled professional worker regardless of proficiency of a newly employed person being in charge of quantitative analysis of the gas components of the gas sample in the sample bag.

The present invention is not limited to the above-mentioned exemplary embodiments but may be variously applied, and may be variously modified by those skilled in the art to which the present invention pertains without departing from the gist of the present invention claimed in the claims.

What is claimed is:

1. An apparatus for quantitatively analyzing gas components with an automatic feed control function of a gas, the apparatus comprising:

a gas chromatograph analyzing a concentration of an introduced gas when the gas is introduced;

a multi-position valve having a plurality of ports and one hole, formed so that when one port is opened, the other ports are all closed, and discharging gas introduced through the port in an open state to the gas chromatograph through the hole;

a pump connected to the gas chromograph and sucking the gas discharged from the hole of the multi-position valve to the gas chromatograph;

a control part obtaining information on an analysis initiation point in time, an analysis termination point in time, and a resting period therebetween from the gas chromatograph, and controlling operations of the pump and the multi-position valve using the information;

a sample bag connected to the port of the multi-position valve and storing a gas sample to be analyzed by the gas chromatograph at a normal pressure;

a high-pressure gas cylinder connected to the port of the multi-position valve and storing a high-pressure standard gas so that the gas chromatograph calculates mole fractions of the gas components of the gas sample;

a gas flowing tube having one end connected to the hole of the multi-position valve and the other end connected to the gas chromatograph to transfer the gas discharged from the hole of the multi-position valve to the gas chromatograph;

a gas pressure regulator provided on the gas flowing tube to regulate a pressure of the gas flowing through the gas flowing tube; and a mass flow rate controller provided between the gas pressure regulator on the gas flowing tube and the gas chromatograph to control a mass flow rate of the gas introduced into the gas chromatograph;

wherein the control part receives a pressure measurement value of the gas sample flowing through the gas flowing tube formed between the mass flow rate controller and the gas chromatograph as a first pressure measurement value as the gas sample stored in the sample bag is introduced into the gas chromatograph, and then receives a pressure measurement value of the standard gas flowing through the gas flowing tube formed between the mass flow rate controller and the gas chromatograph as a second pressure measurement value as the standard gas stored in the high-pressure gas cylinder is introduced into the gas chromatograph, to automatically control suction strength of the pump such that the first pressure measurement value and the second pressure measurement value are within a predetermined error level.

* * * * *